(12) United States Patent
Berkei et al.

(10) Patent No.: US 7,575,734 B2
(45) Date of Patent: Aug. 18, 2009

(54) PROCESS FOR PREPARING DISPERSIBLE SULFATE, PREFERABLY BARIUM SULFATE NANOPARTICLES

(75) Inventors: Michael Berkei, Haltern (DE); Heiner Pfundt, Hamburg (DE)

(73) Assignee: Centrum fur Angewandte Nanotechnologie (CAN) GmbH, Hamburg (DE)

( * ) Notice: Subject to any disclaimer, the term of this patent is extended or adjusted under 35 U.S.C. 154(b) by 199 days.

(21) Appl. No.: 11/579,266

(22) PCT Filed: May 4, 2004

(86) PCT No.: PCT/EP2004/004725

§ 371 (c)(1), (2), (4) Date: Mar. 9, 2007

(87) PCT Pub. No.: WO2005/105933

PCT Pub. Date: Nov. 10, 2005

(65) Prior Publication Data

US 2007/0217992 A1 Sep. 20, 2007

(51) Int. Cl.
*C01B 17/96* (2006.01)
*C01F 5/40* (2006.01)
*C01F 11/46* (2006.01)

(52) U.S. Cl. .................. 423/544; 423/551; 423/554; 106/461; 106/471; 977/773; 977/775

(58) Field of Classification Search ................. 423/544, 423/551, 554; 106/461, 471; 977/773, 775
See application file for complete search history.

(56) References Cited

U.S. PATENT DOCUMENTS

| | | | |
|---|---|---|---|
| 4,894,093 A | | 1/1990 | Aderhold et al. |
| 7,288,239 B2 * | | 10/2007 | Ibarra et al. ................. 423/554 |
| 2003/0124048 A1 | | 7/2003 | Hardinghaus et al. |
| 2003/0159622 A1 * | | 8/2003 | Amirzadeh-Asl et al. ... 106/471 |

FOREIGN PATENT DOCUMENTS

| | | |
|---|---|---|
| CN | 1365993 A | 8/2002 |
| DE | 37 18 277 A1 | 12/1988 |
| DE | 38 10 423 A1 | 10/1989 |
| DE | 100 05 685 A1 | 8/2001 |
| DE | 100 26 791 A1 | 12/2001 |
| DE | 102 29 289 A1 | 1/2004 |
| JP | 58120520 | 7/1983 |
| JP | 2001048533 A | 2/2001 |
| WO | WO 01/07487 A1 | 2/2001 |
| WO | WO 01/58809 A2 | 8/2001 |
| WO | WO 2004/046035 A2 | 6/2004 |

OTHER PUBLICATIONS

Abstract of Japanese Publication No. 06092630 A, published Apr. 5, 1994.
Abstract of Japanese Publication No. 04372712 A, published Dec. 25, 1992.
Summers M. et al., "Formation of $BaSO_4$ Nanoparticles in Microemulsions with Polymerized Surfactant Shells", *Langmuir* 18(12):5023-5026 (2002).
Rees G.D. et al., "Formation and Morphology of Calcium Sulfate Nanoparticles and Nanowires in Water-in-Oil Microemulsions", *Langmuir* 15(6):1993-2002 (1999).

* cited by examiner

*Primary Examiner*—Timothy C Vanoy
(74) *Attorney, Agent, or Firm*—Scully, Scott, Murphy & Presser, P.C.

(57) ABSTRACT

The invention is directed to a process for the manufacture of optionally doped nanoparticulate metal sulfate wherein the metal is selected from polyvalent metals or monovalent transition metals, said process comprising the step of heating a reaction mixture comprising a) a polar organic solvent comprising at least two hydroxy groups or a polar organic solvent comprising at least one sulfoxide group, b) a source of a polyvalent metal or monovalent transition metal, a sulfate source, and optionally a dopant metal source, and c) a base selected from i) bases having an aromatic N-containing heterocycle with the exception of imidazole, ii) bases having an aliphatic N-containing heterocycle, iii) aliphatic hydroxy-substituted amines, iv) aliphatic polyamines, v) aromatic amines, vi) ammonia and ammonia-releasing compounds, and vii) metal hydroxides. The invention is also directed to the resulting metal sulfate nanoparticles.

13 Claims, 2 Drawing Sheets

Fig 1

X-ray diffraction of BaSO₄ nanoparticles in comparison to the data for BaSO₄ bulk material

Fig 2

Particle Size Distribution of $BaSO_4$ nano particles in aqueous dispersion determined by analytical ultra centrifugation

PROCESS FOR PREPARING DISPERSIBLE SULFATE, PREFERABLY BARIUM SULFATE NANOPARTICLES

FIELD OF THE INVENTION

The present invention relates to a method of producing nanoscale sulfate salts with a narrow size distribution. The particles are dispersible in water and methanol without the help of mechanical or chemical dispersing technologies.

BACKGROUND OF THE INVENTION

Barium sulfate is widely used as a white pigment and extender pigment, e.g. in paints, cosmetics and plastics as well as a shadow forming material in x-ray photography or glossing enhancer.

In most applications barium sulfate is needed in the form of a dispersible powder or as a stable colloid dispersion. Due to environmental reasons the main part of paints today is water-based. Thus barium sulfate has to be dispersible in water. To satisfy this demand, U.S. Pat. No. 2,597,384 describes the preparation of colloidal barium sulfate by the reaction of a water soluble sulfate salt with an aqueous barium gluconate solution. However, U.S. Pat. No. 2,597,384 leads to brownish coloured dispersions, which prevent the use as pigment in non-coloured or white applications. Another disadvantage is its high content of water-soluble, toxic barium gluconate.

U.S. Pat. No. 4,551,497 claims the addition of silicate ions to an aqueous slurry of barium sulfate to modify the barium sulfate surface to improve its dispersibility. The resulting particles exhibit a primary particle size of about 0.2 to 20 µm. Thus they are limited to applications where transparency is not required.

To provide smaller particles, it is common practice to mill down natural barium sulfate to an average particle diameter of at least 100 nm. However, these particles can only be dispersed by adding great amounts of dispersants and show no specific benefits, that are expected for nano particles, e.g. narrow size distribution, high uniformity and crystallinity, transparency, etc. DE 10,229,289 offers a method to produce barium sulfate particles with a size of 0.1 to 2 µm. The $d_{50}$ value can be steered in this range by varying the process parameters.

A method for synthesising barium sulfate nano particles with a primary particle size below 100 nm is offered in JP 58,120,520. The barium sulfate particles are prepared in aqueous solution in presence of a water soluble silicate salt to deposit barium silicate on the barium sulfate particles and to inhibit the growth of grains. The resulting product is obtained in form of agglomerates that have to be milled down to their primary particle size. This process leads to additional energy costs in addition to a contamination of the barium sulfate due to abrasion.

A similar primary particle sized barium sulfate is described in US 2003/0124048 A1. The inventors describe a process for producing barium sulfate with a grain size below 100 nm. Furthermore they disclose a method to increase the dispersibility of the barium sulfate by adding dispersing agents or wetting agents during or after the precipitation. Due to interactions of these additives with application media and additional costs, it is however desirable to provide barium sulfate that is dispersible without any additives.

This need exists also for other metal sulfates of commercial interest.

Therefore, an object of this invention is to obviate the above difficulties and to provide a method of producing nanoscale metal sulfates, e.g. barium sulfate, that are dispersible in polar media and solvents, preferably at least in water without the aid of any auxiliary substances, such as disperging agents or specific dispersing techniques.

One further object of the present invention is to provide a method of producing nanoscale metal sulfates, e.g. barium sulfate, that show an excellent degree of whiteness.

According to one preferred embodiment of the invention, a method is to be provided that furnishes nanoscale metal sulfate particles that are at least dispersible in water and methanol without the aid of any auxiliary substances, such as disperging agents and specific dispersing techniques.

SHORT DESCRIPTION OF THE INVENTION

The present invention relates to a process for the manufacture of optionally doped nanoparticulate metal sulfate nanoparticles wherein the metal is selected from polyvalent metals and monovalent transition metals, said process comprising the step of heating a reaction mixture comprising a) a polar organic solvent comprising at least two hydroxy groups or a polar organic solvent comprising at least one sulfoxide group, b) a source of a polyvalent metal or monovalent transition metal, a sulfate source, and optionally a dopant metal source, and c) a base selected from
   i) bases having an aromatic N-containing heterocycle with the exception of imidazole
   ii) bases having an aliphatic N-containing heterocycle,
   iii) aliphatic hydroxy-substituted amines
   iv) aliphatic polyamines
   v) aromatic amines
   vi) ammonia and ammonia-releasing compounds
   vii) metal hydroxides.

The present invention is also directed to the metal sulfates obtainable by this method which preferably have an average size (diameter) measured along their longest axis of 0,5 to 200 nm, more preferably 1 to 50 nm and have their surfaces modified with at least one polar solvent comprising at least two hydroxy groups or at least one sulfoxide group. The resulting sulfate nanoparticles are dispersible at least in water and show a high degree of whiteness.

According to a preferred embodiment of the invention polyvalent metal sulfates or monovalent transition metal sulfates are provided that are dispersible at least in water and methanol. These sulfate nanoparticles have an average size (diameter) measured along their longest axis of 0,5 to 200 nm, preferably 1 to 50 nm and have their surfaces modified with at least one polar solvent comprising at least two hydroxy groups or at least one sulfoxide group.

DETAILED DESCRIPTION OF THE INVENTION

The term "nanoparticulate" is generally understood as referring to particles having an average size of less than 1 µm, i.e. of nm scale. According to the present invention, the particles preferably have an average size measured along their longest axis of 0,5 to 200 nm, more preferably 1 to 50 nm (e.g. 10 to 40 nm). The method of the present invention allows the synthesis of particles having a relatively narrow particle size distribution. Thus, with respect to the above ranges, the standard deviation is preferably less than 40%, in particular less than 35%.

The shape of the nanoparticles produced is not specifically limited and may be needle-like, ellipsoid or spherical, the latter two options being preferred.

Figure 1:
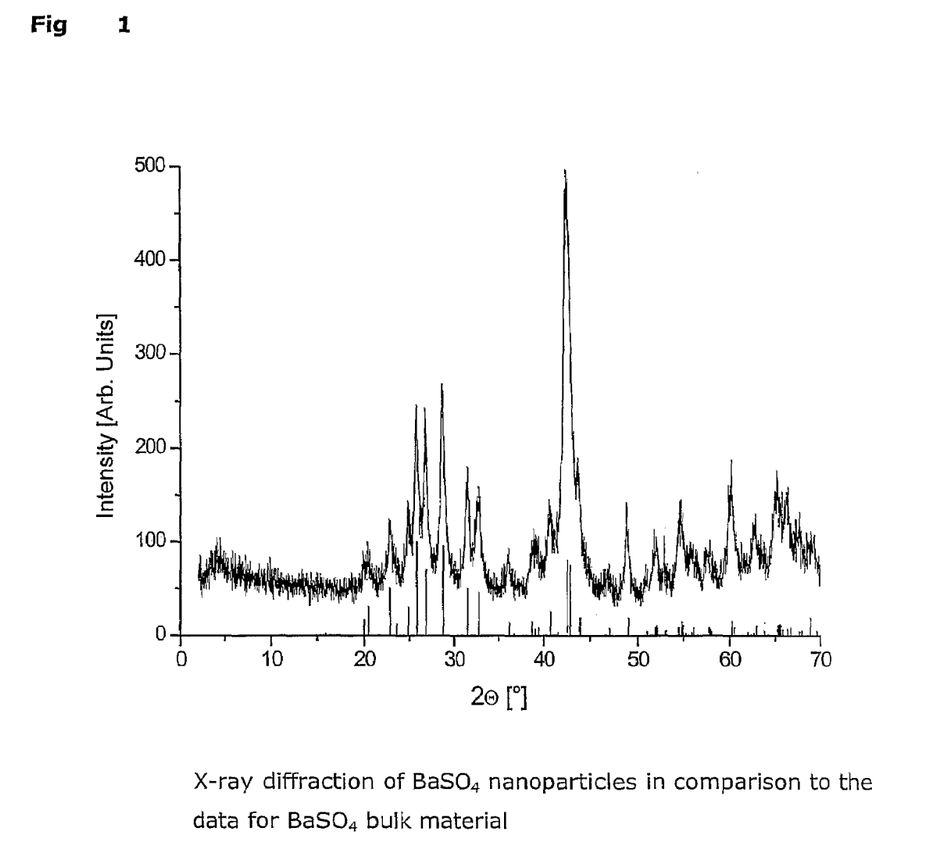
FIG. 1 shows the X-ray diffraction of $BaSO_4$ nanoparticles in accordance with the invention in comparison to data for $BaSO_4$ bulk material.

The nanoparticulate sulfate particles of the invention preferably have a crystalline structure. This can be confirmed by X-ray diffraction measurements of the type shown in FIG. 1 relating to the comparison of $BaSO_4$ nanoparticles in accordance with the invention and $BaSO_4$ bulk material (upper curve: $BaSO_4$ nanoparticles; lower signals: $BaSO_4$ bulk material).

The metal sulfate nanoparticles to be synthesized are preferably sulfates of bi-, tri- or tetravalent metals, such as
  earth alkaline metals, for instance Be, Mg, Ca, Sr or Ba
  sulfates of group 14 metals such as Pb
  sulfates of bi-, tri- or tetravalent transition metals, such as those of group 3 (e.g. La), 4 (e.g. Ti), 5, 6, 7, 8, 9, 10, or 12 (e.g Hg)
  lanthanides, such as Ce, Pr, Nd, Pm, Sm, Eu, Gd, Tb, Dy, Ho, Er, Tm, Yb or Lu, or sulfates of monovalent transition metals such as those of group 11 (e.g. Ag).

Most preferably the metal sulfate is the sulfate of a bivalent metal, in particular an earth alkaline metal sulfate, such as barium sulfate ($BaSO_4$).

In view of the invention's preferred gist to improve water-dispersability, sulfate nanoparticles having a low solubility in water or being water-insoluble are of the greatest interest. Preferably the sulfate to be synthesized has a water-solubility of less than 5 g/100 ml, more preferably less than 1 g/100 ml, in particular less than 0,5 g/100 ml at 20° C.

However, one should emphasize that the present invention is not restricted to sulfate particles having a low solubility in water. Depending on the matrix or solvent, into which the particles are to be incorporated, the surface modification with at least one polar solvent having at least two hydroxy groups or at least one sulfoxide group will enhance the dispersibility irrespective of the particle's water-solubility.

The metal sulfates can be doped with at least one other metal atom in order to impart the metal sulfate specific properties such as luminescence, ferromagnetism, radioactivity or radiopacity. Throughout the present application "doping" is to be understood in a broad sense. Thus, the host material can be substituted by the dopant in an amount of up to 50 mol %, including ranges such as 0.1 to 45 mol %, 0.5 to 40 mol % and 1 to 20 mol %.

Suitable dopant metals involve the following, but are not limited thereto:
  Eu(II), Sn(II), Mn(II), Sb(III), Pb(II), Zn(II), Ti(II), V(II), Cu(II) Cd(II), Ce(III), Sm(III), Pr III), Nd (III), Gd(III), Tb(III), Dy(III), Ho(III), Er (III), Tm(III), Yb(III), Lu(III), Eu (III), Bi(III), Ag(I), Cu(I) or a combination of these dopants, preferably the combination of dopant metal X with dopant metal Y wherein X is selected from Eu(II), Sn(II), Mn(II), Sb(III), Pb(II), Zn(II), Ti(II), V(II), Cu(II), Cd(II) and Y is selected from Ce(III), Sm(III), Pr(III), Nd(III), Gd(III), Tb(III), Dy(III), Ho(III), Er(III), Tm(III), Yb(III), Lu(III), Eu(III), Bi(III), Ag(I) and Cu(I).

The reaction mixture used in the present invention comprises a polar organic solvent comprising at least two hydroxy groups (in the following also referred to as "polyol") and a polar organic solvent comprising at least one sulfoxide group (also referred to as "sulfoxide"). Mixtures of these solvents can also be used.

The term "polar" in connection with the polyol or sulfoxide solvent refers preferably to those solvents which are fully miscible with water at 25° C. independently from the mixing ratio.

The present inventors have found that the use of these polar solvents surprisingly leads to sulfate nanoparticles that show an excellent degree of whiteness and, directly after their synthesis, are dispersible at least in water, preferably at least in water and methanol. In contrast to the prior art, further treatment steps (e.g. milling) or the use of auxiliary chemicals (e.g. dispersing aids) are not necessary for achieving this desired dispersability behaviour. The additional dispersability in methanol can be enhanced by the use of specific bases as explained below in further detail. Without wishing to be bound by theory it is considered that the surface modification of the produced sulfate nanoparticles accounts for these beneficial properties. Thus, it is conceivable that, as far as polyols are concerned, one hydroxy group binds to the nanoparticle surface whereas the other one provides the nanoparticle with sufficient dispersability in water (and methanol). It should be noted that these are only theoretical considerations. At any rate, it is clear that a surface modification takes place since metal sulfate particles of a similar size, which are for instance obtained by grinding macroscopic material, are neither dispersible in water, nor in methanol. It is further believed that the capacity of the polyol or sulfoxide solvent to coordinate to the nanoparticle surface aids in preventing further nanoparticle growth at a relatively early stage of the synthesis thereby ensuring a small and uniform particle size.

Without wishing to be bound by theory, the presence of specific bases in the reaction system also seems to enhance nucleation and control nanoparticle growth. In the majority of cases this may be caused by their capacity to coordinate to and/or chelate the metal atom of the sulfate particle.

In order to test whether or not the produced sulfate nanoparticles show a sufficient dispersability in water or methanol, the following test is conducted. A dry nanoparticle sample weighing 1 g is placed in a 250 ml beaker containing 100 ml distilled water or methanol p.a. under stirring (500 upm) with a magnetic bar (length about 30 mm). After 3 minutes (for water) or 60 minutes (for methanol) of stirring it is observed whether particles deposit on the bottom of the beaker over a time period of 24 hours. If after this period of time the particles do not sediment, they show a sufficient dispersability. "Dispersibility" thus means that a stable homogeneous mixture of solid particles and solvent or medium can be achieved and is to be distinguished from a dissolved state where the ions constituting the sulfate particle dissociate.

The molecular weight of the polyol or sulfoxide solvent is preferably less than 500, more preferably less than 400, even more preferably less than 300, even more preferably less than 200, even more preferably less than 150.

The sulfoxide solvent is preferably a dialkyl sulfoxide, such as dimetholsulfoxide (DMSO).

The polyol is preferably one consisting of carbon, oxygen and hydrogen only. Furthermore, it is preferred that the polyol has two or three hydroxy groups, more preferably two hydroxy groups. The polyol can be selected from glycerol, ethylene glycol or polyethylene glycol whereby preferably low molecular weight polyethylene glycol is used (preferred average number of ethylene glycol units up to 4). Mixtures of polyols may also be used.

Other solvents miscible with the polyol or sulfoxide are not required for conducting the claimed method, but may be present. It is also permissible that water is present. However, it would appear that too high water contents may adversely affect the dispersibility of the particles produced. Therefore, it is preferred to adjust the weight ratio (polyol or sulfoxide)/water to more than 50, more than 60, more than 70, more than 80, more than 90 and more than 95 with increasing preference.

Suitable metal atom sources are soluble or dispersible in the reaction mixture, e.g. the metal nitrates or halides (chlorides, bromides, iodides) and the corresponding hydrates. This applies equally to host and dopant metal atoms. It is preferred to use the chlorides. If other metal salts are used, care should be taken that these are soluble or dispersible in the reaction mixture under reaction conditions.

Similarly, the sulfate source should be soluble or dispersible under reaction conditions. Preferred starting materials for the sulfate are alkali metal (hydrogen)sulfates, ammonium (hydrogen)sulfates or (hydrogen)sulfates having an organic cation as counter ion. The use of hydrogensulfates ($HSO_4-$) is preferred. The organic cation is preferably selected from basic N-containing aliphatic, aromatic and aliphatic/aromatic substances which have preferably from 4 to 30, more preferably from 4 to 20 carbon atoms. Suitable cations involve for instance quaternary ammonium or phosphonium wherein the four substituents can be independently selected from alkyl having preferably from 1 to 10 carbon atoms (preferably 1 to 5) or benzyl, or protonated aliphatic bases, such as amantadinium, protonated aromatic bases or hydrazinium.

Suitable hydrogensulfates can for instance be selected from tetrabutylammonium hydrogensulfate, tetramethylammonium hydrogensulfate, bis-tetrabutylammonium hydrogensulfate, triethylammonium hydrogensulfate, ammonium hydrogensulfate, sodium or potassium hydrogensulfate, amantadinium hydrogensulfate, hydrazinium hydrogensulfate, ammonium hydrogensulfate being preferred.

According to the present invention the base to be used is selected from the following embodiments:

i) Bases having an aromatic N-containing heterocycle with the exception of imidazole, preferably bases having an aromatic N-containing 5- or 6-membered heteromonocycle such a pyrol, pyrazole, isoxazole, isothiazole, oxazole, thiazole, 1,2,4-triazole, 1,2,4-oxadiazole, 1,2,4-thiadiazole pyridine, pyridazine, pyrimidine, pyrazine, 1,2,3-triazine, 1,2,4-triazine, 1,3,5-triazine. Preferably the N-atom is the only heteroatom. The most preferred embodiment thereof is pyridine. These heterocycles may be substituted, preferably by at least one substituent selected from halide (F, Cl, Br, J), $C_{1-4}$-alkyl (preferably methyl), —$NR_2$, —NHR, —$NH_2$, —OH, —OR, —OCOR, —NHCOR, —NHCHO, —$NRCONR'_2$, —$C_{5-10}$-aryl wherein R is
$C_{1-4}$-alkyl (e.g. methyl) and R' is H or $C_{1-4}$-alkyl (e.g. methyl). The N-containing heterocycle may also display more than one (e.g. two or three) substituents of the same or different type. The type and position of substituents is preferably selected such that they do not sterically shield the basic N-atom and further do not reduce its basicity to an undesired extent. One preferred example for substituted N-containing heterocycles is collidine (2,4,6-trimethylpryridine). The total carbon number of the optionally substituted base is preferably 2 to 20, more preferably 3 to 15, e.g. 4 to 12.

ii) Bases having a saturated or partially unsaturated aliphatic N-containing heterocycle, preferably bases having an aliphatic N-containing 5- or 6 membered heteromonocycle, such as pyrrolidine, imidazolidine, piperidine, piperazine or other saturated or partially unsaturated derivatives of the above-mentioned aromatic N-containing heterocycles. These heterocycles, if substituted, may also carry at least one of the aforementioned substituents. Among these bases, the use of pyrrolidine or piperidine is preferred. The total carbon number of the optionally substituted base is preferably 2 to 20, more preferably 3 to 15, e.g. 4 to 12.

iii) Aliphatic hydroxy-substituted amines, preferably alkylamines having from 2 to 10 carbon atoms, more preferably from 2 to 5 carbon atoms, in particular two or three carbon atoms wherein the hydroxy group is preferably located at the opposite end of the alkyl chain with respect to the position of the amino group ($\alpha$, $\omega$-substitution). The most preferred embodiment of this base type is ethanolamine.

iv) Aliphatic polyamines, preferably $\alpha$, $\omega$-substituted diamines having from 2 to 20 carbon atoms, more preferably 2 to 5 carbon atoms, in particular 2 or 3 carbon atoms, such as ethylenediamine.

v) Aromatic amines, preferably those wherein the aromatic structure has from 6 to 10 carbon atoms as in aniline (aminobenzene). If being substituted, the aromatic amine, preferably the aniline may carry at least one of the aforementioned substituents, preferably at least one amino- or alkyl-substituent as in o-phenylenediamine or o-toluidine.

vi) Ammonia and compounds known to release ammonia at higher temperatures, specifically the reaction temperature of the method according to the invention, such as urea and urea derivatives.

vii) Metal hydroxides, preferably alkali metal hydroxides such as NaOH or KOH.

The afore-mentioned amines can also be generated in situ by the Hoffmann degradation of the corresponding quaternary ammonium compounds under suitable reaction conditions as known in the art.

Among these bases, it is preferred to use
i) bases having an aromatic N-containing heterocycle, such as optionally substituted pyridine (e.g. pyridine or collidine),
ii) bases having a saturated or partially unsaturated aliphatic N-containing heterocycle, preferably bases having an aliphatic N-containing 5- or 6 membered heteromonocycle, such as pyrrolidine and in particular piperidine.
iii) aliphatic hydroxy-substituted amines, such as alkanolamine, or
vi) ammonia-releasing compounds, such as urea and urea derivatives
v) o-toluidine as it was found that these lead to metal sulfate nanoparticles that are not only dispersible in water, but also show a surprisingly good dispersability in methanol. This behaviour represents a major technological advantage since it may render post-modification steps as explained below redundant and increases the compatibility of the nanoparticles obtained with less polar solvents and matrix systems.

If pyridine, collidine or ethylenediamine is used as a base, the claimed method
a) can for instance be conducted to prepare undoped bivalent metal sulfates, in particular $BaSO_4$.
b) Pyridine, collidine or ethylenediamine are preferably added as such, i.e. not in protonated form since this may require pH adaptations and further could include possibly undesired counter ions in the reaction mixture.
c) If pyridine, collidine or ethylenediamine is used as base, the preferred sulfate source is any of the hydrogensulfates described below.
d) The preferred pH ranges given for the claimed method also apply to the use of ethylenediamine, pyridine and collidine.
e) Similarly, ethyleneglycol is also the most preferred solvent, if pyridine, collidine or ethylenediamine are used as base.

These five embodiments may also be used in combinations of at least two.

According to one further embodiment of the present invention it is possible to exclude $BaSO_4$ having an average particle size of 19 nm and being produced in glycerol and imidazol at 70° C. from the claimed particles.

Preferably the reaction is conducted as follows. The metal source, optionally also the dopant metal source, preferably the corresponding chlorides are dissolved in a polyol or sulfoxide solvent followed by the addition of at least one of the above bases. Preferably, the solution of the metal source(s) is heated prior to the addition of the base. Separately, the sulfate source, preferably a hydrogensulfate such as ammonium hydrogensulfate is dissolved in a polyol or sulfoxide solvent (preferably the same as used for the first solution). To start the reaction, the solution of the sulfate source is preferably added to the solution of the metal source under stirring.

The reaction can be conducted at temperatures ranging from 50 to 240° C., depending from the reaction time. However, one advantage of the claimed method resides in that relatively low temperatures from 60 to 100° C., preferably 70 to 90° C., can be used irrespective of the type of solvent employed. This is economically beneficial and increases the degree of whiteness of the nanoparticles obtained, presumably since less colored byproducts are formed.

Metal source and sulfate source are preferably used in approximately stoichiometric ratios, preferably in a mol ratio metal/sulfate ranging from 1.2/1 to 0.8/1, more preferably 1.1/1 to 0.9/1, most preferably 1.05/1 to 0.95/1.

Furthermore, it has turned out to be beneficial if the base is used in molar amounts of 0.3 to 0.7, preferably 0.4 to 0.6, most preferably 0.45 to 0.55 based on the metal source.

The pH of the reaction preferably ranges from 2 to 9, more preferably 3 to 7, most preferably 4 to 6.

Depending on the reaction temperature and system, relatively short reaction times of for instance 10 min up to longer reaction times of several hours are suitable for conducting the claimed method. Preferably reaction times from 30 min to 2 hours are used.

Upon completion of the reaction, the reaction mixture is cooled to room temperature. The precipitation of sulfate particles can be enhanced by the addition of methanol. The resulting sulfate nanoparticles are preferably separated by centrifugation and washed with a suitable solvent, such as methanol.

The size of the resulting nanoparticles can be determined by conventional techniques, such as ultra-centrifugation or transmission electron micrography (TEM). Prior to the analytical ultra-centrifugation, it may be checked by means of TEM or also XRD measurings whether the particles are present in the non-aggregated state, in order to prevent a falsification of the measured results.

Figure 2:
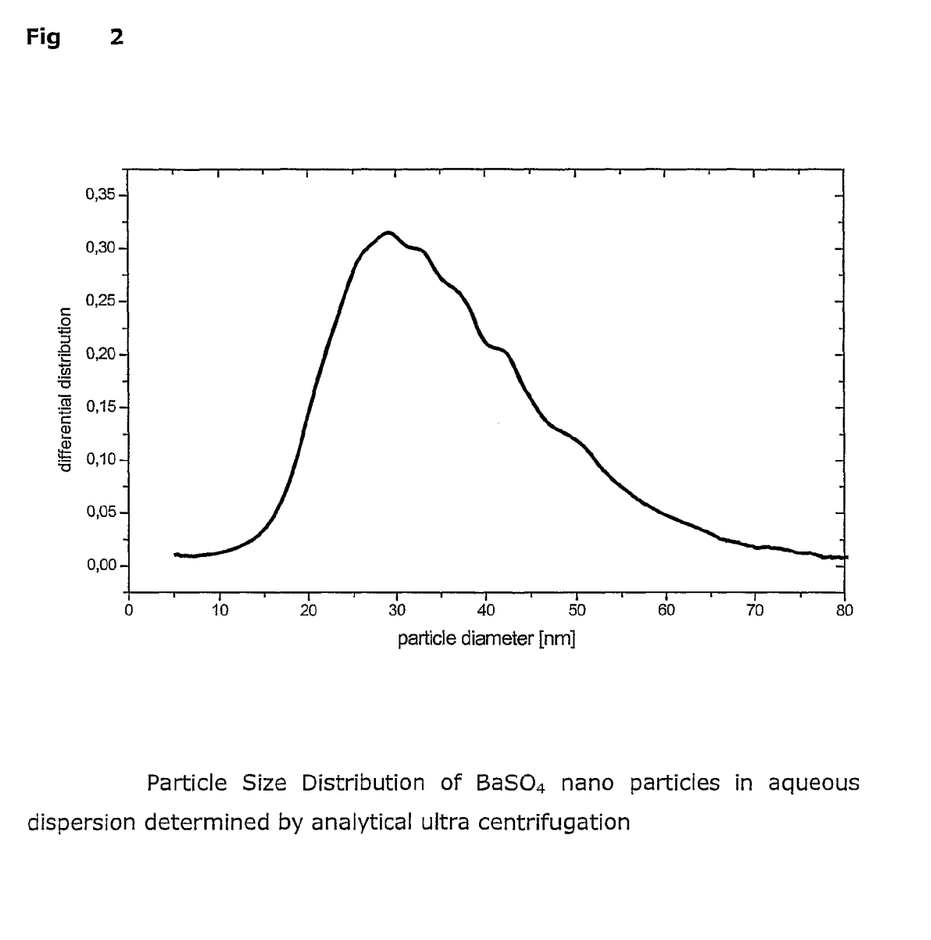
FIG. 2 shows a typical particles size distribution of $BaSO_4$ nanoparticles according to the invention determined by analytical ultracentrifugation with an aqueous dispersion of the particles.

FIG. 2 shows a typical particles size distribution of $BaSO_4$ nanoparticles according to the invention determined by analytical ultracentrifugation with an aqueous dispersion (concentration 1 wt. %) of the particles, (particle density was supposed to be 4.5 g/cm$^3$). The average of the Gauss distribution was 31 nm with a standard deviation of 31%.

The same technique of course can also be used for monitoring growth in samples of the reaction mixture.

The particles produced according to this method are dispersible in water and, according to one preferred and claimed embodiment, also in methanol. The water and methanol-dispersible particles are preferably synthesized as indicated before.

Dispersions of the nanoparticles according to the invention in water or methanol are not subject to any specific limitations regarding the nanoparticle concentration. Surprisingly, it has been found that higher concentrations rather appear to enhance the stability of the dispersion. Dispersions containing up to about 1 wt % of nanoparticles are transparent. With increasing nanoparticle content the dispersions then adopt a translucent or opalescent appearance while still no precipitation or sedimentation takes place. Even dispersions containing 30 wt % of sulfate nanoparticles, specifically barium sulfate nanoparticles were found to be stable over an extended period of time of several weeks. Further increasing the concentration will finally lead to a pasty mass.

The water- and methanol-dispersible particles have an average size measured along their longest axis of 1 to 200 nm and a particle surface modified with at least one polar solvent having at least two hydroxy groups or at least one sulfoxide group, as explained above. Other properties have also been described.

It should be stressed that the fact that the nanoparticles produced were tested only for their dispersability in water and methanol does not exclude that they also show dispersability in other solvents. If however, the dispersability in other solvents or specific media is found to be insufficient, post-modification techniques can be carried out as follows. Thus, it is for instance possible to modify the surface of the nanoparticles by heating these in at least one coordinating solvent selected from P-organic compounds as described in WO 02/20696 A1, such as tris(2-ethylhexyl)phosphate (TEHP) or tributylphosphte (TBP); mono- or dialkyl amines of the type described in this WO reference such as dodecylamine; carbonic acids; alcohols; organic esters; silanes; siloxanes; organic sulfones of the formula R—S($O_2$)—R'; organic ketones of the formula R—(C=O)—R'; organic nitrites (RCN), organic sulfoxides (R—S(O)—R'), organic amides (R—(C=O)—NR'R'') or sulfonamides R—S($O_2$)—NR'R'') wherein R R' and R'' are selected independently from aliphatic residues, preferably alkyl, having from 1 to 20 carbon atoms or aromatic residues, such as phenyl, having from 6 to 20, preferably from 6 to 10 carbon atoms. Partially fluorinated or perfluorinated variants of these can be used for achieving a surface modification that leads to sulfate nanoparticles being readily dispersible in fluoropolymers or fluorinated solvents. The above surface modification techniques allow the incorporation of sulfate nanoparticles obtainable by the claimed method into a huge variety of solvents and matrices including polymers such as olefin-based polymers, silicone polymers, fluorinated polymers and products of daily use such as lacquers or paints. The surface-modified sulfate nanoparticles can be homogenously and finely dispersed in these systems without specific dispersion techniques or dispergent aids.

Sulfate nanoparticles produced according to the invention, specifically those produced in a polyol, are further particularly suitable for post-synthesis modification techniques further enhancing the dispersability and compatibility with organic matrices, in particular polymer matrices. Thus, it is possible to subject the second hydroxy group (i.e. the one being not linked to the particle surface) to chemical reactions which either modify the compatibility with a specific medium wherein the particle is to be incorporated and/or link monomers thereto that can be chemically bound in a polymer matrix by polymerisation reactions. One suitable example for these modification techniques involves the reaction with silane coupling agents which may carry a monomeric group.

Non-toxic sulfate nanoparticles that were produced in accordance with the present invention can be directly (without further surface-modification) used for diagnostic purposes. This is of particular interest for heavy metal sulfates, such as barium sulfate, which is widely used in the medicinal field as a contrast agent. Due to their small size and excellent dispersability behavior, these sulfate nanoparticles can be administered intravenously since they will be homogenously distributed in the human or animal body and do not clog venae, arteriae and other blood vessels. Barium sulfate or other sulfate nanoparticles doped with paramagnetic or radioactive elements thus can be used as extremely versatile tool for in vivo diagnostics.

EXAMPLES

The present invention is now further illustrated by the following examples.

Example 1

Preparation of Barium Sulfate with Pyridine in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml ethylene glycol at r.t. and heated to 80° C. To this solution 0.8 ml (10 mmol) pyridine was added (solution A).

During this time 2.304 g (20 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of about 90%. The particles are dispersible in water and methanol and exhibit an average particle size of 35 nm in aqueous dispersion, determined by analytical ultra centrifugation.

Example 2

Preparation of Barium Sulfate with Urea in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml Ethylene glycol at r.t. and heated to 80° C. To this solution 0.6 g (10 mmol) urea was added (solution A).

During this time 2.304 g (20 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 87%. The particles are dispersible in water and methanol.

Example 3

Preparation of Barium Sulfate with 2,4,6-Trimethyl Pyridine in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml Ethylene glycol at r.t. and heated to 80° C. To this solution 1.212 g (10 mmol) 2,4,6-trimethyl pyridine was added (solution A).

During this time 2.304 g (20 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of about 84%. The particles are dispersible in water and methanol.

Example 4

Preparation of Barium Sulfate with Ethylen Diamine in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml Ethylene glycol at r.t. and heated to 80° C. To this solution 0.68 ml (10 mmol) ethylene diamine was added (solution A).

During this time 2.304 g (20 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 75%. The particles are dispersible in water.

Example 5

Preparation of Barium Sulfate with Pyrrolidine in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml Ethylene-glycol at r.t. and heated to 80° C. To this solution 0.827 ml (10 mmol) pyrrolidine was added (solution A).

During this time 2.304 g (20 mmol) NH$_4$HSO$_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of about 90%. The particles are dispersible in water and slightly dispersible in methanol.

Example 6

Preparation of Barium Sulfate with Piperidine in Ethylene Glycol

In a 50 ml three neck round bottom flask, equipped with a thermometer, a reflux condenser and a magnetic stirrer (PTFE), 5.081 g (20.8 mmol) BaCl$_2$×2H$_2$O was dissolved in 24.8 ml Ethylene glycol at r.t. and heated to 60° C. To this solution 0.41 ml (10 mmol) piperidine was added (solution A).

During this time 2.304 g (20 mmol) NH$_4$HSO$_4$ was dissolved in 8.4 ml Ethylene glycol and heated to 60° C. (solution B). To start the reaction, solution B was added to solution A under stirring and the reaction mixture was stirred for 1 hour at 60° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 84%. The particles are dispersible in water and methanol, but precipitate during 8 hours.

Example 7

Preparation of Barium Sulfate with Aniline in Ethylene Glycol

In a 50 ml three neck round bottom flask, equipped with a thermometer, a reflux condenser and a magnetic stirrer (PTFE), 5.081 g (20.8 mmol) BaCl$_2$×2H$_2$O was dissolved in 24.8 ml Ethylene glycol at r.t. and heated to 80° C. To this solution 0.93 mg (10 mmol) aniline was added (solution A).

During this time 2.304 g (20 mmol) NH$_4$HSO$_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 92%. The particles are dispersible in water.

Example 8

Preparation of Barium Sulfate with o-Phenylen Diamine in Ethylene Glycol

In a 50 ml three neck round bottom flask, equipped with a thermometer, a reflux condenser and a magnetic stirrer (PTFE), 5.081 g (20.8 mmol) BaCl$_2$×2H$_2$O was dissolved in 24.8 ml Ethylene glycol at r.t. and heated to 80° C. To this solution 1.082 g (10 mmol) o-phenylen diamin was added (solution A).

During this time 2.304 g (20 mmol) NH$_4$HSO$_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 98%. The particles are dispersible in water.

Example 9

Preparation of Barium Sulfate with o-Toluidine in Ethylene Glycol

In a 50 ml three neck round bottom flask, equipped with a thermometer, a reflux condenser and a magnetic stirrer (PTFE), 5.081 g (20.8 mmol) BaCl$_2$×2H$_2$O was dissolved in 24.8 ml Ethylene glycol at r.t. and heated to 80° C. To this solution 0.11 ml (10 mmol) o-toluidine was added (solution A).

During this time 2.304 g (20 mmol) NH$_4$HSO$_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 98%. The particles are dispersible in water and precipitate during 16 hours. Furthermore they are slightly dispersible in methanol and ethanol.

Example 10

Preparation of Barium Sulfate with Sodium Hydroxide in Ethylene Glycol

In a 50 ml three neck round bottom flask, equipped with a thermometer, a reflux condenser and a magnetic stirrer (PTFE), 5.081 g (20.8 mmol) BaCl$_2$×2H$_2$O was dissolved in 24.8 ml Ethylene glycol at r.t. and heated to 80° C. To this solution 4 drops of a 1 molar sodium hydroxide solutions was added (solution A) and the pH adjusted to 9.

During this time 2.304 g (20 mmol) NH$_4$HSO$_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 78%. The particles are dispersible in water and slightly dispersible in methanol and precipitate during 16 hours.

Example 11

Preparation of Barium Sulfate with Ammonia in Ethylene Glycol

In a 50 ml three neck round bottom flask, equipped with a thermometer, a reflux condenser and a magnetic stirrer (PTFE), 5.082 g (20.8 mmol) $BaCl_2 \times 2H_2O$ was dissolved in 24.8 ml ethylene glycol at r.t. and heated to 80° C. To this solution 2 drops of ammonia (25% in water) was added (solution A) and the pH adjusted to pH=9.

During this time 2.304 g (20 mmol) $NH_4HSO_4$ was dissolved in 8.4 ml ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 75%. The particles are dispersible in water and slightly dispersible in methanol and precipitate during 16 hours.

Example 12

Preparation of Barium Sulfate with Ethanol Amine in Ethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml Ethylene glycol at r.t. and heated to 80° C. To this solution 0.6 ml (10 mmol) ethanol amine was added (solution A).

During this time 2.304 g (20 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 99%. The particles are dispersible in water and methanol.

Example 13

Preparation of Barium Sulfate with Pyridine in Ethylene Glycol and an Access of Sulfate Ions In a 50 ml three neck round bottom flask, equipped with a thermometer, a reflux condenser and a magnetic stirrer (PTFE), 4.886 g (20 mmol) $BaCl_2 \times 2H_2O$ was dissolved in 24.8 ml Ethylene glycol at r.t. and heated to 80° C. To this solution 0.8 ml (10 mmol) pyridine was added (solution A).

During this time 2.422 g (21 mmol) $NH_4HSO_4$ was dissolved in 8.4 ml Ethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 100%. The particles are dispersible in water and methanol and exhibit an average particle size of 35 nm.

Example 14

Preparation of Barium Sulfate with Pyridine in Ethylene Glycol:Glycerol (95:5)

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in a mixture of 23.6 ml Ethylene glycol and 1,75 ml glycerol at r.t. and heated to 80° C. to this solution 0.8 ml (10 mmol) pyridine was added (solution A).

During this time 2.304 g (20 mmol) $NH_4HSO_4$ was dissolved in 8 ml Ethylene glycol and heated to 80° C. (solution B). To start the reaction, solution B was added to solution A under stirring and the reaction mixture was stirred for 1 hour at 80° C. After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of about 99%. The particles are dispersible in water and methanol.

Example 15

Preparation of Barium Sulfate with Pyridine in Diethylene Glycol

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml diethylene glycol at r.t. and heated to 80° C. To this solution 0.8 ml (10 mmol) pyridine was added (solution A).

During this time 2.304 g (20 mmol) $NH_4HSO_4$ was dissolved in 8.4 ml diethylene glycol and heated to 80° C. (solution B). To start the reaction, solution B was added to solution A under stirring and the reaction mixture was stirred for 1 hour at 80° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., white barium sulfate nano particles were obtained with a yield of 96%. The particles are dispersible in water and methanol.

Comparative Example 1

Preparation of Barium Sulfate with Imidazol in Ethylene Glycol

In a 50 ml three neck round bottom flask, equipped with a thermometer, a reflux condenser and a magnetic stirrer (PTFE), 1.343 g (5.5 mmol) $BaCl_2 \times 2H_2O$ was dissolved in 21 ml ethylene glycol at r.t. To this solution 0.340 g (5 mmol) imidazole was added (solution A).

During this time 0.578 g (5 mmol) $NH_4HSO_4$ was dissolved in 4.5 ml ethylene glycol at r.t. (solution B). To start the reaction, solution B was added to solution A under stirring and the reaction mixture was heated to 180° C. and stirred for 2 hours at 180° C.

After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed two times with 30 ml of methanol. After drying in vacuum at r.t., pale beige barium sulfate nanoparticles were obtained with a yield of about 97%. The particles are dispersible in water.

Comparative Example 2

Preparation of Barium Sulfate with Pyridine in Water

In a 50 ml three neck round bottom flask, equipped with a thermometer, a reflux condenser and a magnetic stirrer (PTFE), 5.081 g (20.8 mmol) $BaCl_2 \times 2H_2O$ was dissolved in 24.8 ml water at r.t. and heated to 80° C. To this solution 0.8 ml (10 mmol) pyridine was added (solution A).

During this time 2.304 g (20 mmol) $NH_4HSO_4$ was dissolved in 8.4 ml water and heated to 80° C. (solution B). To start the reaction, solution B was added to solution A under stirring and the reaction mixture was stirred for 1 hour at 80° C. After this time the reaction slurry was cooled to about 30° C. and spiked with 35 ml methanol to precipitate the barium sulfate particles and to lower the viscosity of the slurry. The resulting barium sulfate was separated by centrifugation (5 min, 18000 upm) and washed-two times with 30 ml of methanol. After drying in vacuum at r.t., white barium sulfate nano particles were obtained with a yield of about 90%. The particles are almost non-dispersible in water and start to precipitate directly after stirring in water.

While the invention has been described in detail and with reference to specific embodiments thereof, it will be apparent to one skilled in the art that various changes and modifications can be made therein without departing from the spirit and scope thereof.

The invention claimed is:

1. A process for the manufacture of optionally doped nanoparticulate metal sulfate nanoparticles wherein the metal is selected from polyvalent metals or monovalent transition metals, said process comprising the step of heating a reaction mixture comprising
    a) a polar organic solvent comprising at least two hydroxy groups or a polar organic solvent comprising at least one sulfoxide group,
    b) a source of a polyvalent metal or monovalent transition metal, that is a salt of a polyvalent metal or monovalent transition metal, a sulfate source, and optionally a dopant metal source, and
    c) a base selected from
        i) bases having an aromatic N-containing heterocycle with the exception of imidazole,
        ii) bases having an aliphatic N-containing heterocycle,
        iii) aliphatic hydroxy-substituted amines,
        iv) aliphatic polyamines,
        v) aromatic amines,
        vi) ammonia and ammonia-releasing compounds, and
        vii) alkali metal hydroxides.

2. The process according to claim 1, wherein the base is selected from
    i) bases having an aromatic N-containing 5- or 6-membered heteromonocycle,
    ii) bases having an aliphatic N-containing 5- or 6-membered heteromonocycle,
    iii) aliphatic hydroxy-substituted amines,
    iv) aliphatic diamines having 2 to 10 carbon atoms,
    v) aniline, or alkyl- or amino-substituted derivatives thereof,
    vi) ammonia and urea, and
    vii) alkaline metal hydroxides.

3. The process according to claim 1, wherein the base is selected from bases having an aromatic N-containing heterocycle, urea and urea derivatives, o-toluidine, aliphatic hydroxy-substituted amities and bases having an aliphatic N-containing heteromonocycle.

4. The process according to claim 3, wherein the reaction is carried out in the presence of ethylene glycol as polar solvent.

5. The process according to claim 4, wherein the reaction is carried out at a temperature from 60 to 100° C.

6. The process according to claim 5, wherein the polyvalent metal sulfate is an alkaline earth metal sulfate.

7. The process according to claim 4, wherein the polyvalent metal sulfate is an alkaline earth metal sulfate.

8. The process according to any of claims 1 to 3, wherein the reaction is carried out at a pH from 2 to 9.

9. The process according to claim 1, wherein the reaction is carried out in the presence of ethylene glycol as polar solvent.

10. The process according to claim 1, wherein the reaction is carried out at a temperature from 60 to 100° C.

11. The process according to claim 1 wherein the polyvalent sulfate is an earth alkaline metal sulfate.

12. Optionally doped polyvalent metal sulfates or monovalent transition metals sulfates obtainable by the method of claim 1 having an average size measured along their longest axis of 1 to 50 nm wherein their surfaces are modified with at least one polar solvent comprising at least two hydroxy groups or at least one sulfoxide group.

13. Optionally doped polyvalent metal sulfates or monovalent transition metals sulfates having an average size measured along their longest axis of 1 to 50 nm which have their surfaces modified with at least one polar solvent comprising at least two hydroxy groups or at least one sulfoxide group and are dispersible in water and methanol.

* * * * *